US006868345B1

(12) United States Patent
Jensen

(10) Patent No.: US 6,868,345 B1
(45) Date of Patent: Mar. 15, 2005

(54) MONITORING AUDITORY EVOKED POTENTIALS

(75) Inventor: Erik Weber Jensen, San Pol De Mar (ES)

(73) Assignee: Danmeter A/S (DK)

( * ) Notice: Subject to any disclaimer, the term of this patent is extended or adjusted under 35 U.S.C. 154(b) by 23 days.

(21) Appl. No.: 10/239,772

(22) PCT Filed: Nov. 15, 2000

(86) PCT No.: PCT/DK00/00636

§ 371 (c)(1),
(2), (4) Date: Feb. 5, 2003

(87) PCT Pub. No.: WO01/74248

PCT Pub. Date: Oct. 11, 2001

(30) Foreign Application Priority Data

Mar. 31, 2000 (DK) ........................................ 2000 00537

(51) Int. Cl.[7] ................................................ G06F 3/00
(52) U.S. Cl. ........................ 702/32; 702/31; 702/188; 702/189
(58) Field of Search ............................. 702/31, 32, 39, 702/56, 179, 188, 189, 103, 111; 128/731; 600/544

(56) References Cited

U.S. PATENT DOCUMENTS

| | | | |
|---|---|---|---|
| 5,697,379 A | * | 12/1997 | Neely et al. ................. 600/544 |
| 6,196,977 B1 | * | 3/2001 | Sininger et al. ............. 600/559 |
| 6,493,576 B1 | * | 12/2002 | Dankwart-Eder ........... 600/544 |
| 6,556,861 B1 | * | 4/2003 | Prichep ....................... 600/544 |

FOREIGN PATENT DOCUMENTS

| | | | |
|---|---|---|---|
| HU | 215 658 B | 3/1994 | |
| WO | WO 98/10701 | 3/1998 | ............ A61B/5/11 |

OTHER PUBLICATIONS

Jensen, et al. "Definition of a Depth of Anaesthesia Index Using Fuzzy Inductive Reasoning (FIR).", Proceedings of the First Joint BMES/EMBS Conference Serving Humanity, Advancing Technology, Oct. 13–16, '99, Atlanta, GA, p. 920. (IEEE).

Jensen, et al. "On–line Analysis of Middle Latency Auditory Evoked Potentials (MLAEP) for Monitoring Depth of Anaesthesia in Laboratory Rats", Medical Engineering & Physics 20, (1998), pp. 722–728.

Elkfafi, et al., "Intelligent Signal Processing of Evoked Potentials for Anaesthesia Monitoring and Control", IEE Proc.–Control Theory Appl., vol. 144, No. 4, Jul. 1997, pp. 354–360.

* cited by examiner

Primary Examiner—Patrick Assouad
Assistant Examiner—Felix Suarez
(74) Attorney, Agent, or Firm—Fulwider Patton Lee & Utecht, LLP

(57) ABSTRACT

A method and an apparatus for extracting signals which are indicative of the level of consciousness of a patient comprises subjecting the patient to a repetitive audio stimulus, monitoring AEP produced by the patient using an autoregressive model with exogenous input, and then calculating an index (AAI), which is displayed or used otherwise, indicative of the anaesthetic depth.

35 Claims, 2 Drawing Sheets

MONITORING AUDITORY EVOKED POTENTIALS

BACKGROUND OF THE INVENTION

The present invention relates to an apparatus for extracting signals which are indicative of the level of consciousness of a patient comprising means for monitoring auditory evoked potentials (AEP) produced by the patient as a response to a repetitive acoustic click stimulus, means for extracting an AEP within a few repetitions, preferably more than 10 and less than 50 of the audio stimulus, means for using an autoregressive model with exogenous input (ARX), and means for calculating an index (AAI) indicative of anaesthetic.

Assessment of depth of anaesthesia is in general based on clinical observations of physiologic parameters such as blood pressure, heart beat rate, pupil size etc. The use of neuro-muscular blocking agents during general anaesthesia disables the clinical signs that normally indicate consciousness. A number of incidents exist where patients describe that they were fully conscious during the surgery, and in the worst case had perception of pain and cardiac arrhythmias. Hence, there is a need for a method and apparatus to assess the anaesthetic depth. A number of investigation results have already been published, where Auditory Evoked Potentials (AEP) are used to indicate the level of consciousness during general anaesthesia. The AEP is a sub-component of the EEG signal, and it is elicited by acoustic stimuli and is recorded with scalp electrodes, amplified and analysed by a computer. The AEP is an electrical, small signal embedded in noise from the ongoing EEG, and for this reason advanced signal processing is necessary to extract the AEP signals. The AEP signals are traditionally extracted by the averaging of up to 1000 repetitions of the response of the stimuli signals. This is a very time-consuming process, which takes up to several minutes to carry out, typically 2–3 minutes, which is excessive if the anaesthesiologist has to use the AEP signals as a predictor of an adequate anaesthetic dose.

From international patent application no. WO 98/10701 (PCT/GB97/02435) a control system and a method for calculating an index representation of the depth of anaesthesia are known. The method of calculating an index indication of anaesthetic depth is based on monitoring AEP produced by the patient and providing a signal corresponding to the coarseness of the monitored AEP signal. The raw AEP signal is divided into a series of sweeps or frames of a given duration, each sweep being synchronised with the repetitive audio stimuli. A number of sweeps n are recorded in sequence and are averaged to produce a time average sweep. The anaesthesia index is calculated for the time-averaged sweep. Each time a new series of sweeps is recorded, a new time-averaged sweep is determined from the most resent n sweeps, and the anaesthesia index for that time-averaged sweep is calculated. In this way the index is constantly updated.

It has been observed that when a patient loses consciousness, the amplitudes of most AEP peaks are reduced and their latencies are generally also increased. These changes occur almost simultaneously and in the same direction with all patients. Therefore, a suitable index is one, which reflects these changes.

An empirical algorithm has been developed for calculating the index, which algorithm is based upon the sum of the square roots of the difference between every two successive points in the moving time-averaged sweep. This auditory evoked potential index is given by the following equation:

$$AEP = k \sum_{i=1}^{255} \sqrt{|x_i - x_{i+1}|}$$

where $x_1$ to $x_{256}$ are the sample points of the time-averaged frame and k is a scaling constant.

The AEP index is calculated for every filtered time-averaged sweep, and a plot of the index against time can be generated for display and on a screen. When the patient is awake, the index is typically in the range of 80 to 90, whereas during anaesthesia it is typically in the range of 35 to 40.

An article in "Methods of Information in Medicine", 1996; 35: 256–260, with the title: "Autoregressive Modeling with Exogenous Input of Middle-Latency Auditory-Evoked Potentials to Measure Rapid Changes in Depth of Anesthesia" by E. W. Jensen, P. Lindholm and S. W. Henneberg describe a system identification method, an autoregressive model with exogenous input (ARX), to produce a sweep-by-sweep estimate of the AEP. The method was clinically evaluated in 10 patients anaesthetized with alfentanil and propofol. The time interval between propofol induction and the time when the Na—Pa amplitude was decreased to 25% of the Initial amplitude was measured. These measurements showed that ARX-estimated compared to MTA-estimated AEP was significantly faster in tracing transition from consciousness to unconsciousness during propofol induction ($p<0.05$).

It is the object of the invention to improve this measuring method in such a manner that a safer result is achieved considerably more rapidly, whereby the risk of treating a patient, e.g. by surgery, without full anaesthetization is reduced.

The delay is reduced to about 6 seconds by using ARX modelling.

It is a second object of the invention to make the procedure for anaesthetization more effective (time-efficient) and to reduce the staff workload.

It is a third object of the invention to produce an apparatus for continuous monitoring of the level of consciousness, which apparatus is portable and easy to install and operate.

This is achieved by using an apparatus as disclosed in claim 1.

Further advantageous characteristics are achieved by that which is disclosed in the dependent claims.

With the apparatus according to the invention the possibility is achieved of extracting the AEP with only a few repetitions, often as low as 15, which reduces the delay to approximately 6 seconds. As the AEP is a very complex signal comprising several peaks and troughs, it is desirable to map the AEP into a single number—an ARX index of easy interpretation, but containing the same information as the AEP. This is possible by following the method and by using the apparatus according to the invention. The ARX index is typically larger than 60 when the patient is awake, and decreases when the patient is anaesthetized; a loss of consciousness will typically occur when the index gets below 28.

The apparatus according to the invention can operate only with three surface electrodes, e.g. three propritary surface electrodes, the result being:

Fully updated AEP available within few seconds.

Significantly faster calculating AEP index than the traditional Moving Time Average method.

Significantly faster at tracing transition from unconsciousness and vice versa.

Consistent, accurate readings.

Possible optimised display for use in operating theatre.

Touch screen—easy to operate and clean.

Fully graphic display

The apparatus according to the invention monitor the level of consciousness during general anaesthesia independently of the biological variation of the patients with respect to tolerance and sensitivity of the anaesthetics.

The calculations according to the invention can be performed on a computer as disclosed in claims 8 and 9.

BRIEF DESCRIPTION OF THE DRAWINGS

The invention will now be described in more detail with reference to the drawings, in which.

DETAILED DESCRIPTION OF THE PREFERRED EMBODIMENT

Figure 1:
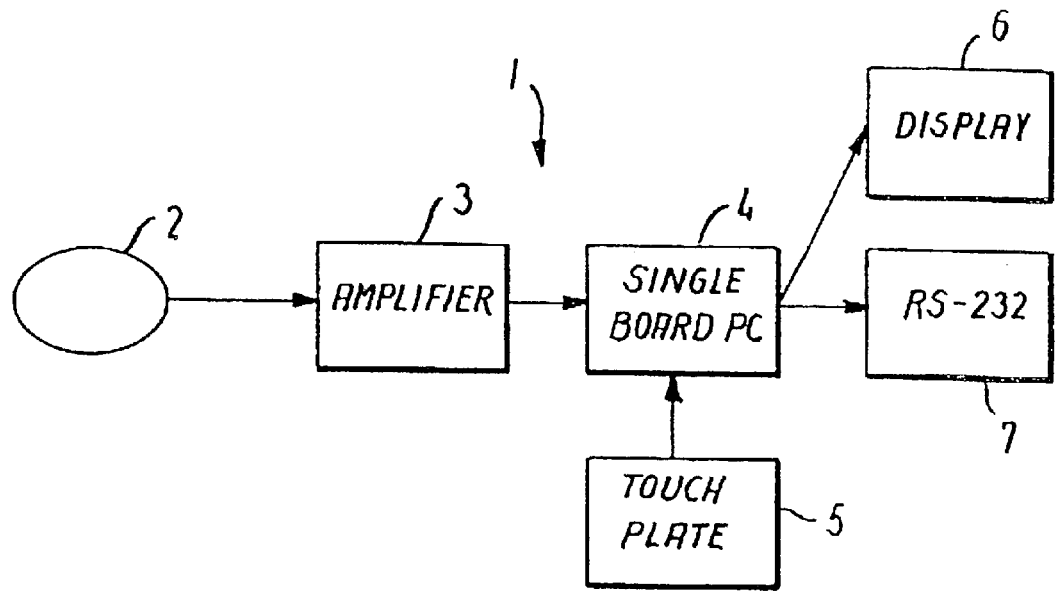
FIG. 1 shows a schematic view of an embodiment of a system of the present invention for extracting the AEP (auditory evoked potentials) and for calculating an index.

In FIG. 1 is schematically shown a system 1 for extracting the AEP (auditory evoked potentials) and for calculating an index, which is indicative of the depth of anaesthesia of a patient.

The patient 2 is subjected to repetitive sound signals, which are delivered to the patient by headphones, earphones or the like. These sound signals are in the form of "clicking" noise signals of short duration, approximately 1–2 ms, which are delivered to both ears of the patient, and which produces distinctive potentials, known as AEP or auditory evoked potentials in the electroencephalographic (EEG) response of the patient. The headphones and the equipment for producing the sound signals, e.g. a signal generator, are not shown in FIG. 1.

Electrodes, with which EEG-signals (electroencephalographic signals) are provided, are attached to the head of the patient 2. Three or more electrodes, e.g. scalp electrodes, may be used. If three electrodes are used, they are attached to the patient 2 at the following positions: A positive electrode at the middle forehead, a reference electrode at the left forehead and a negative electrode behind the ear, preferably in the region of the mastoid process. Other positions may be used with similar results.

The electrodes are connected to a patient cable, which leads to an amplifier 3. This amplifier 3 is an instrumentation amplifier with a high common mode rejection ratio (CMMR). The amplified analogue signal is digitised by an A/D-converter (not shown) before being led to a digital processing unit 4. This digital unit may be in the form of a personal computer (PC), in particular a single board personal computer. The digitised signal is analysed and stored on the computer 4, which is programmed according to algorithms for extracting the AEP (auditory evoked potentials) and according to algorithms for calculation of an index. These methods for extracting the AEP and for calculating the index shall later be described in further detail.

The AEP and the index are displayed on a display 6, and with an input device 5 is it possible to give instructions to the computer 4. This input device 5 may be in the form of a touch plate or a touch screen, which can be combined with the display 6, in which way it will be possible to give instructions to the computer by touching the display.

The extracted and calculated values of the Index and the AEP-signals can be transmitted to external equipment (not shown) using a connection 7, which connection may be in the form of a RS-232 connection. The external equipment may for example be apparatus for administering drugs to the patient. Thus the system can be used for controlling the amount of drug being delivered to the patient in relation to the depth of anaesthesia. Other examples of external equipment are apparatus for monitoring or for treating the patient, for example apparatus for controlling the respiratory system.

The procedures or functions included in a method and a system, called the A-line-monitor (AAI: A-line ARX Index), according to an embodiment of the invention is shown in the diagram in FIG. 2

The data representing the signals from the patient is introduced to the processing unit 4 in the form of a series of raw sweeps 11. In an embodiment of the invention these sweeps 11 are provided at a sampling frequency of 900 Hz, and each sweep consists of 70 samples, giving a sweep length of 80 ms. The dick stimulus used for producing the signals was of 2 ms duration and of an intensity of 70 dB above normal hearing level.

Each sweep is initially processed by an artifact algorithm 12 in order to decide whether the sweep should be included for further processing. Two types of artifact algorithms are used.

First, when artefacts are present in a sweep the amplitude of the raw data will in general be much larger than the amplitude of normal sweeps. The amplitude, expressed as a range of numbers, allowed of the A/D-converter, is for example 0–65534. The 95% EEG range is 15000–55000, hence if a sample is below 5000 or above 60000 a number of subsequent samples, e.g. 400 samples are rejected.

Second, during periods after saturation of the amplifier 3 the signal will move in to a normal range, i.e. 15000–55000. However in this period a click artifact arising from the acoustic stimulus may be observed. Hence an algorithm that detects the click-artifact is implemented. The mean deference of the 10 samples before the click is calculated. If the difference between the first sample in a sweep n and the last sample in the sweep n−1 is larger than for example five times the previous calculated mean difference, hence a number of subsequent samples, e.g. the next 800 samples, are rejected.

In order to improve the signal-to-noise ratio (SNR) a band pass filter 13 is included in the system previous to the application of the moving timer average (MTA) and the autoregressive with exogenous input (ARX) model. The filter, which in an embodiment of the invention has a band pass from 16 to 150 Hz, may be a fifth order Butterworth filter, which is digitally implemented.

The ARX model (autoregressive with exogenous input), with which a rapid extraction of the AEP is facilitated, shall now be described with reference to FIG. 3, which shows a generalised ARX model.

The ARX model is obtained by adding an exogenous input to the AR model for analysing digital signals. Hence the ARX model is defined by the following equation:

$$y(t)+a_1 \cdot y(t-1)+ \ldots +a_n \cdot y(t-n)=b_1 \cdot u(t)+ \ldots +b_m \cdot u(t-m+1)+e$$

where n is the order of the backwards coefficients ($a_1 \ldots a_n$) and m is the order of the forward coefficients ($b_1 \ldots b_m$). The output is y, u is the exogenous input and e is the error.

Figure 3:
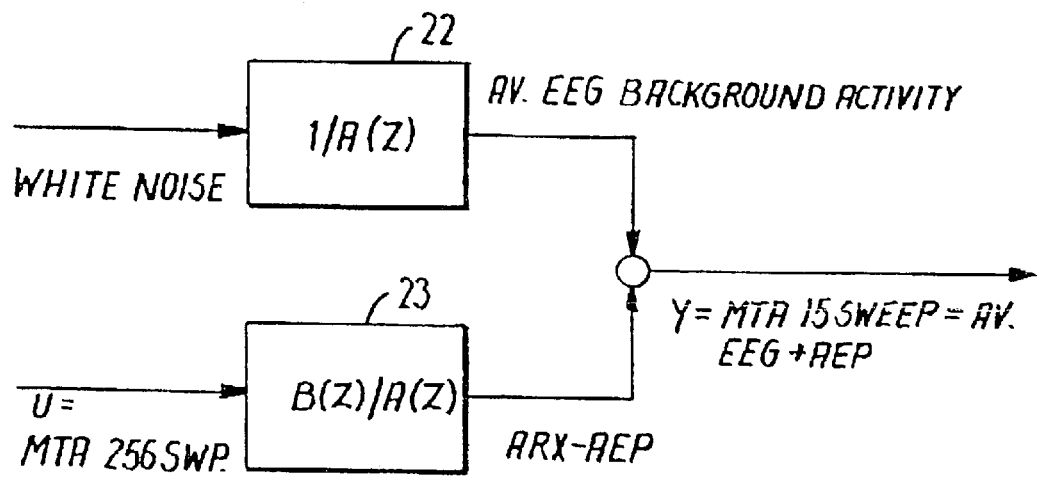
FIG. 3 shows a block diagram illustrating the generalised ARX model (autoregressive with exogenous input), which is used according to the invention.

On FIG. 3 is shown the AR-part 22, which is driven by white noise and is defined by the averaged EEG activity Pre-averaging may be done using 15 sweeps.

The exogenous input u to the block 23 is an AEP produced by averaging a number of sweeps, for example the latest 256 sweeps. The output y from the ARX model is an average of a number, preferably 15, of the latest collected sweeps consisting of averaged EEG background activity and AEP. When the coefficients of the model are determined, the ARX-AEP is obtained by IIR filtering of the exogenous Input u.

With a model order of for example five, the ARX equations are the following $$y_6 = -a_1 y_5 - \ldots - a_5 y_1 + b_1 u_6 + \ldots + b_5 u_2 + e$$

$$y_8 = -a_1 y_6 - \ldots - a_5 y_2 + b_7 u_7 + \ldots + b_5 u_3 + e$$

$$y_{70} = -a_1 y_{69} - \ldots - a_5 y_{65} + b_1 u_{70} + \ldots + b_5 u_{56} + e$$

The error terms, e, are omitted and the equations are written on matrix form:

$$\begin{pmatrix} -y_5 & -y_4 & -y_3 & -y_2 & -y_1 & u_6 & u_5 & u_4 & u_3 & u_2 \\ -y_6 & -y_5 & -y_4 & -y_3 & -y_2 & u_7 & u_6 & u_5 & u_4 & u_3 \\ \vdots & \vdots & \vdots & \vdots & \vdots & \vdots & \vdots & \vdots & \vdots & \vdots \\ -y_{69} & -y_{68} & -y_{67} & -y_{66} & -y_{65} & u_{70} & u_{69} & u_{68} & u_{67} & u_{66} \end{pmatrix} \begin{pmatrix} a_1 \\ \vdots \\ a_5 \\ b_1 \\ \vdots \\ b_5 \end{pmatrix} = \begin{pmatrix} y_6 \\ y_7 \\ \vdots \\ y_{10} \end{pmatrix}$$

The equation system shown above is an over determined set of linear equations. Hence Gaussean elimination or LU-decomposition will fail to give a satisfactory result. A very powerful way to solve an over determined system is the singular value decomposition (SVD), which solves the problem in a least mean squares (LMS) sense. Singularities in a matrix, which means that the matrix does not have a full rank, often occur when the matrix is composed of data with no clear a priori knowledge. The singularity can occur if here is an ambiguity in the equations. This is a paradox because on the one hand the system is over determined (more equations than unknowns) and at the same time it is undetermined because too many equations are linear (or close to linear) combinations of each other. SVD not only diagnoses and solves the singularity problems and produces a meaningful numerical result but it also provides the LMS solution.

The model order is determined by considering the error function. The error function is defined by $$L = \frac{1}{N} \sum_{i=1}^{N} e(i)^2$$

where e(i)=y(i)=y(i)−yˆ(i) and N the number of samples in one sweep. The variables y(i) and yˆ(i) are the real and the predicted pre-average of a number of sweeps, for example 15 sweeps, respectively. The identification is tested by Andersons test on whiteness of the prediction error, e. If the prediction error is white at a confidence level of 95% the ident is accepted. The optimal values of n and m are selected by minimising the final prediction error (FPE) function defined by Akaike (Akaike H."Statistical predictor identification", Ann. Inst. Statist. Math, 1970; No. 22, pp 203–217):

$$FPE = L \cdot (N+n+1)/(N-n-1)$$

where n is the total number of coefficients of the ARX model.

FPE represents a need of minimising the error function and the need of limiting the number of parameters of the ARX model.

The order of the ARX model should ideally be calculated for each sweep. This is a very time consuming process. hence to comply with the need of fast processing time an average model order of five for both backward- and forward coefficients was chosen. It is obvious that another suitable number may be chosen, preferably a number less than 10.

Figure 2:
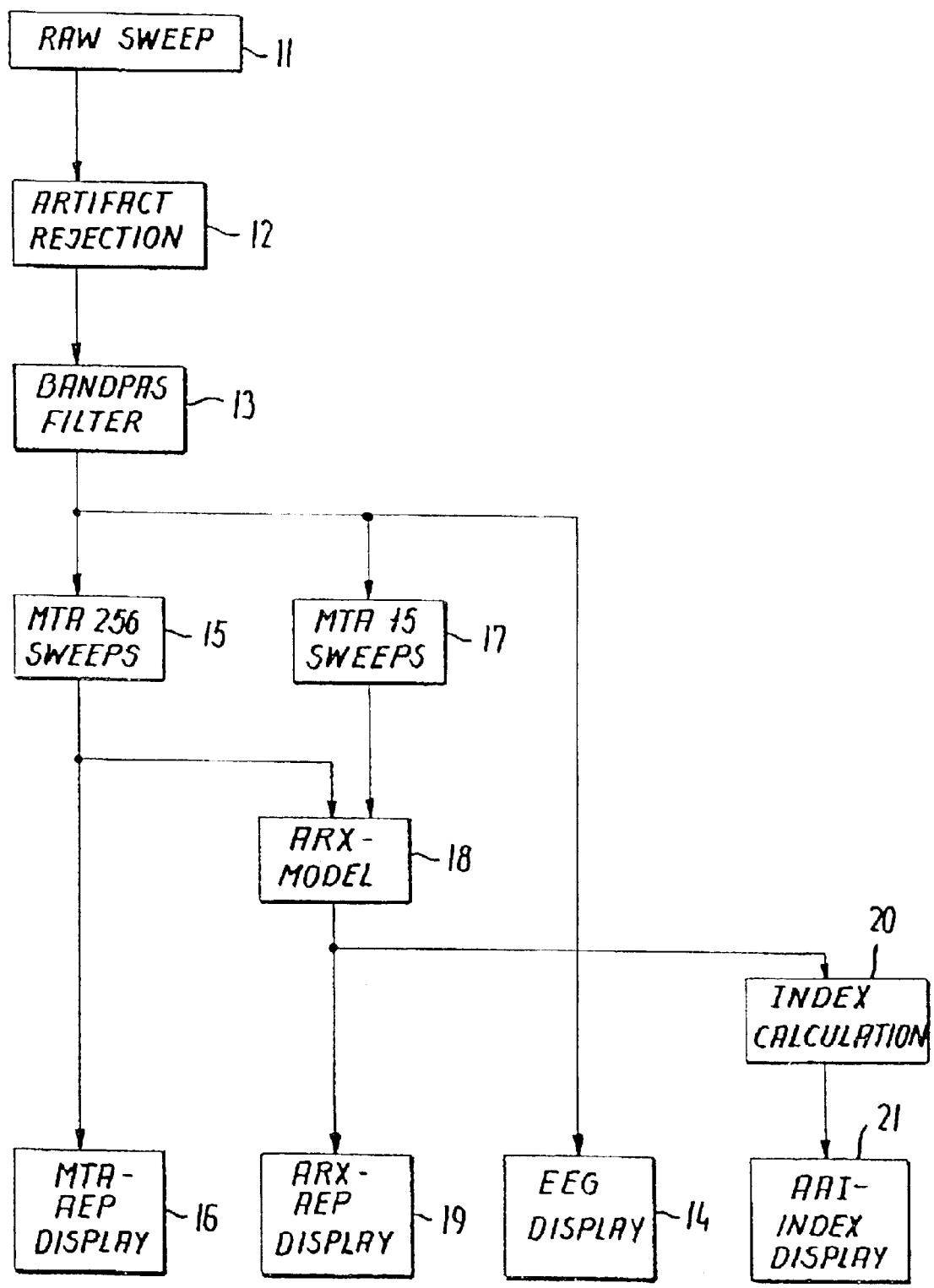
FIG. 2 shows a block diagram with the necessary procedures to provide the extraction and index calculation of the AEP (auditory evoked potentials) according to an embodiment of the invention.

As shown on FIG. 2, the output from the block 15, which is the AEP achieved by an moving time average (MTA) calculated over 256 sweeps with each sweep weighted equally, is led to the display 6 (FIG. 1), where it may be displayed as an $AEP_{MTA}$-display 16. Further the output from the band pass filter 13, i.e. the EEG-signal, is led to the display 6 (FIG. 1). where it may be displayed as an EEG-display 14.

The output from the block 15 is also led to the ARX model 16 together with the output from the output from the block 17, which produces a MTA over a minor number of sweeps, preferably 15 sweeps: The output from the ARX model 18, which as explained above is an AEP extracted by the ARX and which is called an $AEP_{ARX}$, is also led to the display unit 6 (FIG. 1), where it may be displayed as an $AEP_{ARX}$-display 19.

In order to quantify the level of anaesthesia It is desirable to map the $AEP_{ARX}$ Into an index. In order to do this, the output from the ARX model is led to a block 20 for index calculation, the function of which shall be explained in the following.

The index calculated by the block 20 is called the A-line ARX-index (AAI) and may be displayed on the display unit 6 (FIG. 1), where it may be displayed as an AAI-($AEP_{ARX}$-) index display 21. The AEP consists of several peaks. It is generally accepted that the amplitudes of the peaks with latency 10–100 ms, corresponding to the middle latency AEP (MLAEP), decreases when the patient is anaesthetized and at the same time the latencies of the peaks are prolonged. The index according to the invention preserves these two rules in order not to lose information. Furthermore in order to achieve a reliable index the following premises are complied with:

1. Validity for the largest number of patients possible, independent of surgery and aesthetic drugs.
2. Good dynamics is required between awake and asleep state in order to distinguish awareness changes from noise.

The AEP-index is calculated in a window of the AEP, which may preclude the start and the end of the window. Preferably the window is the 20–80 ms window of the AEP and latency and amplitude changes in the AEP is weighted equally. The 20 ms start of the window is chosen not to include BAEP (Brainstem Auditory Evoked Potentials) and auricular muscular artefacts and the 80 ms end of the window is chosen in order not to include LLAEP. This is because BAEP and LLAEP (Long Latency Auditory Evoked Potentials) do not correlate well to anaesthetic depth. The AEP index (AAI) according to the invention has shown good discrimination between conscious and anaesthetized patients in previous studies. The AEP-index (AAI) is defined to reflect the hypnotic level during anaesthesia. First y is defined as:

$$y = k_1 \sum_{i=k_2}^{k_3} |x_i - x_{i+1}|$$

where $x_i$ are the samples of a sweep,
$k_1$ are a constant, which preferably is larger than 0.0100 and less than 0.02000, and which in particular may be chosen to be 0.0165, and
where $k_2$ and $k_3$ are the start and the end samples, respectively, of the summation, chosen not to include the start and the end of the AEP window.

If the AEP window consists of 70 samples, $k_2$ may preferably be 17, and $k_3$ may be 69.

The AAI-index is defined as:

$$AAI-\text{index} = \begin{cases} k_1 \sum_{i=k_2}^{k_3} |x_i - x_{i+1}| \\ \text{if } y > 60 \Rightarrow k_4 y + k_5 \\ \text{if } y < 15 \text{ and } y > 4 \Rightarrow k_6 + k_7 \times e^{y/p} \end{cases}$$

where $k_4$, $k_5$, $k_6$, $k_7$ and p are constants.
Preferably $0.2500 < k_4 < 0.3000$, and in a most preferred form $k_4 = 0.2786$.
Preferably $43.0000 < k_5 < 43.5000$, and in a most preferred form $k_5 = 43.2857$.
Preferably $9.1000 < k_6 < 9.8000$, and in a most preferred form $k_6 = 9.3769$.
Preferably $0.25 < k_7 < 0.30$, and in a most preferred form $k_7 = 0.28$.
Preferably $4 \leq p \leq 6$, and in a most preferred form p=5.

In the most preferred embodiment of the invention the ARX Index is defined as:

$$AAI-\text{index} = \begin{cases} 0.0165 \sum_{i=17}^{69} |x_i - x_{i+1}| \\ \text{if } y > 60 \Rightarrow 0.2786 y + 43.2857 \\ \text{if } y < 15 \text{ and } y > 4 \Rightarrow 9.3769 + 0.28 \times e^{y/5} \end{cases}$$

The index is in the range of 0 to 99, where increasing value indicates elevated level of consciousness.

The apparatus according to the invention may essentially be performed on a computer 4, e.g. a Single Board computer with 486 MHz clock frequency and provided with programming with matching software, e.g. using the programming language Borland Pascal, so that the algorithms or parts thereof, which are explained in the description and disclosed in the claims, are performed in such a manner that the desired result is achieved, i.e. calculation and display of the AAI-index explained above. The program according to the invention is storable on any known type of computer readable medium, so that it is easily installed in the computer 4.

What is claimed is:

1. An apparatus for extracting signals which are indicative of the level of consciousness of a patient comprising means for monitoring auditory evoked potentials (AEP) produced by the patient as a response to a repetitive acoustic click stimulus, means for extracting an AEP within a few repetitions, preferably more than 10 and less than 50 of the audio stimulus, means for using an autoregressive model with exogenous input (ARX), and means for calculating an index (AAI) indicative of anaesthetic, characterized in that the index is defined as:

$$AAI-\text{index} = \begin{cases} k_1 \sum_{i=k_2}^{k_3} |x_i - x_{i+1}| \\ \text{if } y > 60 \Rightarrow k_4 y + k_5 \\ \text{if } y < 15 \text{ and } y > 4 \Rightarrow k_6 + k_7 \times e^{\frac{y}{p}} \end{cases}$$

where k4, $k_5$, k6, $k_7$ and p are constants, and where y is defined as:

$$y = k_1 \sum_{i=k_2}^{k_3} |x_i + x_{i+1}|$$

where $x_1$ are the samples of a sweep,
$k_1$ are a constant, which preferably is larger than 0.0100 and less than 0.02000, and which in particular may be chosen to be 0.0165, and where $k_2$ and $k_3$ are the start and the end samples, respectively, of the summation, chosen not to include the start and the end of the AEP window, or that the index is defined as:

$$AAI-\text{index} = \begin{cases} 0.0165 \sum_{i=17}^{69} |x_i - x_{i+1}| \\ \text{if } y > 60 \Rightarrow 0.2786 y + 43.2857 \\ \text{if } y < 15 \text{ and } y > 4 \Rightarrow 9.3769 + 0.28 \times e^{\frac{y}{5}}. \end{cases}$$

2. An apparatus according to claim 1, characterized in that it further comprises means for filtering the AEP signals, preferably a band pass filter with a band pass from 16 to 150 Hz, and preferably a digitally implemented Butterworth filter of fifth order.

3. An apparatus according to claims 1–2, characterized in that only signals in an AEP window consisting of about 100 ms (milliseconds) are used in calculating the index, preferably a window of 20–80 ms precluding the start and the end of the sweep.

4. An apparatus according to claim 1, characterized in that the AEP window consists of maximum 80 samples, and in that $k_2$ may preferably be 17, and in that $k_3$ may preferably be 69.

5. An apparatus according to claim 1, characterized in that $k_4$, $k_5$, $k_6$, $k_7$ and p are defined as follows:
preferably $0.2500 < k_4 < 0.3000$, and in a most preferred form $k_4 = 0.2786$.
preferably $43.0000 < k_5 > 43.5000$, and in a most preferred form $k_5 = 43.2857$
preferably $9.1000 < k_6 < 9.8000$, and in a most preferred form $k_6 = 9.3769$
preferably $0.25 < k_7 < 0.30$, and in a most preferred form $k_7 = 0.28$
preferably $4 \leq p \leq 6$, and in a most preferred form p=5.

6. An apparatus according to claim 1. characterized in that it comprises means for providing sweeps at a sampling frequency of about 700–1000 Hz, preferably about 900 Hz, and an AEP window of maximum 100 ms, in that only signals within the window are used in calculating the index, preferably a window of 20–80 ms precluding the start and the end of the sweep.

7. An apparatus according to claim 1. characterized in that it comprises means to display or to signal the calculated index (AAI).

8. A computer program comprising computer programming code means adapted to perform all the calculations claim 1, when said program is run on a computer.

9. A computer program as claimed in claim 8 and embodied on a computer readable medium.

10. An apparatus according to claim 2, characterized in that the AEP window consists of maximum 80 samples, and in that $k_2$ may preferably be 17, and in that $k_3$ may preferably be 69.

11. An apparatus according to claim 3, characterized in that the AEP window consists of maximum 80 samples, and in that $k_2$ may preferably be 17, and in that $k_3$ may preferably be 69.

12. An apparatus according to claim 2, characterized in that $k_4, k_5, k_6, k_7$ and p are defined as follows:
preferably $0.2500 < k_4 < 0.3000$, and in a most preferred form $k_4 = 0.2786$.
preferably $43.0000 < k_5 > 43.5000$, and in a most preferred form $k_5 = 43.2857$,
preferably $9.1000 < k_6 < 9.8000$, and in a most preferred form $k_6 = 9.3769$
preferably $0.25 < k_7 < 0.30$, and in a most preferred form $k_7 = 0.28$.
preferably $4 \leq p \leq 6$, and in a most preferred form p=5.

13. An apparatus according to claim 3, characterized in that $k_4, k_5, k_6, k_7$ and p are defined as follows:
preferably $0.2500 < k_4 < 0.3000$, and in a most preferred form $k_4 = 0,2786$.
preferably $43.0000 < k_5 > 43.5000$, and in a most preferred form $k_5 = 43,2857$.
preferably $9.1000 < k_6 < 9.8000$, and in a most preferred form $k_6 = 9.3769$
preferably $0.25 < k_7 < 0.30$, and in a most preferred form $k_7 = 0,28$.
preferably $4 \leq p \leq 6$, and in a most preferred form p=5.

14. An apparatus according to claim 4, characterized in that $k_4, k_5, k_6, k_7$ and p are defined as follows:
preferably $0.2500 < k_4 < 0.3000$, and in a most preferred form $k_4 = 0.2786$.
preferably $43.0000 < k_5 > 43.5000$, and in a most preferred form $k_5 = 43,2857$,
preferably $9.1000 < k_6 < 9.8000$, and in a most preferred form $k_6 = 9.3769$
preferably $0.25 < k_7 < 0.30$, and in a most preferred form $k_7 = 0.28$.
preferably $4 \leq p \leq 6$, and in a most preferred form p =5.

15. An apparatus according to claim 2, characterized in that it comprises means for providing sweeps at a sampling frequency of about 700–1000 Hz, preferably 900 Hz, and an AEP window of maximum 100 ms, in that only signals within the window are used in calculating the index, preferably a window of 20–80 ms precluding the start and the end of the sweep.

16. An apparatus according to claim 3, characterized in that it comprises means for providing sweeps at a sampling frequency of about 700–1000 Hz, preferably about 900 Hz, and an AEP window of maximum 100 ms, in that only signals within the window are used in calculating the index, preferably a window of 20–80 Ms precluding the start and the end of the sweep.

17. An apparatus according to claim 4, characterized in that it comprises means for providing sweeps at a sampling frequency of about 700–1000 Hz, preferably about 900 Hz, and an AEP window of maximum 100 ms, in that only signals within the window are used in calculating the index, preferably a window of 20–80 Ms precluding the start and the end of the sweep.

18. An apparatus according to claim 5, characterized in that it comprises means for providing sweeps at a sampling frequency of about 700–1000 Hz, preferably about 900 Hz, and an AEP window of maximum 100 ms, in that only signals within the window are used in calculating the index, preferably a window of 20–80 ms precluding the start and the end of the sweep.

19. An apparatus according to claim 2, characterized in that it comprises means to display or to signal the calculated index (AAI).

20. An apparatus according to claim 3, characterized in that it comprises means to display or to signal the calculated index (AAI).

21. An apparatus according to claim 4, characterized in that it comprises means to display or to signal the calculated index (AAI).

22. An apparatus according to claim 5, characterized in that it comprises means to display or to signal the calculated index (AAI).

23. An apparatus according to claim 6, characterized in that it comprises means to display or to signal the calculated index (AAI).

24. A computer program comprising computer programming code means adapted to perform all the calculations in claim 2 when said program is run on a computer.

25. A computer program comprising computer programming code means adapted to perform all the calculations in claim 3 when said program is run on a computer.

26. A computer program comprising computer programming code means adapted to perform all the calculations in claim 4 when said program is run on a computer.

27. A computer program comprising computer programming code means adapted to perform all the calculations in claims 5 when said program is run on a computer.

28. A computer program comprising computer programming code means adapted to perform all the calculations in claim 6 when said program is run on a computer.

29. A computer program comprising computer programming code means adapted to perform all the calculations in claim 7 when said program is run on a computer.

30. A computer program as claimed in claim 24 and embodied on a computer readable medium.

31. A computer program as claimed in claim 25 and embodied on a computer readable medium.

32. A computer program as claimed in claim 26 and embodied on a computer readable medium.

33. A computer program as claimed in claim 27 and embodied on a computer readable medium.

34. A computer program as claimed in claim 28 and embodied on a computer readable medium.

35. A computer program as claimed in claim 29 and embodied on a computer readable medium.

* * * * *

UNITED STATES PATENT AND TRADEMARK OFFICE
CERTIFICATE OF CORRECTION

PATENT NO. : 6,868,345 B1
DATED : March 15, 2005
INVENTOR(S) : Erik Weber Jensen It is certified that error appears in the above-identified patent and that said Letters Patent is hereby corrected as shown below:

Column 1,
Line 55, delete "resent" and insert -- recent --.

Column 2,
Line 26, delete "Initial" and insert -- initial --.

Column 5,
Line 11, delete "Input" and insert -- input --.
Line 16, delete "$y_8$" and insert -- $y_7$ --.
Line 39, delete "here" and insert -- there --.
Line 61, delete "ident" and insert -- identification --.

Column 6,
Line 23, delete "16" and insert -- 18 --.
Line 30, delete "It is" and insert -- it is --.
Line 31, delete "Into an index" and insert -- into an index --.

Column 8,
Lines 55 and 62, delete "." (period) after "claim 1".
Line 66, after "all the calculations" insert -- in --.

Column 9,
Line 14, delete "0.2786." and insert -- 0.2786, --.
Line 19, after "9.3769" insert -- , -- (comma).
Line 21, delete "0.28." and insert -- 0.28, --.
Line 26, delete "0,2786." and insert -- 0.2786, --.
Line 28, delete "43,2857." and insert -- 43.2857, --.
Line 30, after "9.3769" insert -- , -- (comma).
Line 33, delete "0,28." and insert -- 0.28, --.
Line 38, delete "0.2786." and insert -- 0.2786, --.
Line 40, delete "43,2857" and insert -- 43.2857 --.
Line 42, after "9.3769" insert -- , -- (comma).

UNITED STATES PATENT AND TRADEMARK OFFICE
CERTIFICATE OF CORRECTION

PATENT NO. : 6,868,345 B1
DATED : March 15, 2005
INVENTOR(S) : Erik Weber Jensen It is certified that error appears in the above-identified patent and that said Letters Patent is hereby corrected as shown below:

Column 9 (cont'd),
Line 45, delete "0.28." and insert -- 0.28, --.

Signed and Sealed this

Twenty-fourth Day of January, 2006

JON W. DUDAS
*Director of the United States Patent and Trademark Office*